United States Patent [19]
Lin et al.

[11] Patent Number: 5,972,327
[45] Date of Patent: Oct. 26, 1999

[54] METHOD OF TREATING ALLERGIC RHINITIS BY DELIVERING MEDICATION VIA THE NASAL VESTIBULES

[76] Inventors: Matthew M. Lin; Audrey H. Lin, both of 100 Pace Dr. S., West Islip, N.Y. 11795

[21] Appl. No.: 08/955,963

[22] Filed: Oct. 22, 1997

[51] Int. Cl.$^6$ ...................................................... A61K 9/06
[52] U.S. Cl. ...................... 424/78.05; 514/887; 514/937; 514/944; 514/969
[58] Field of Search ................................... 424/45, 78.05; 514/887, 937, 944, 969

[56] References Cited

U.S. PATENT DOCUMENTS 4,124,707  11/1978  Green et al. ........................ 424/78.03
4,250,163  2/1981  Nagai et al. .......................... 424/78.03

OTHER PUBLICATIONS

Health News Daily (1993); vol. 5, Issue 132.
JAMA (1997). vol. 278, No. 22, pp. 1842–1847.
Berkow et al. (1992). The Merck Manual. Merck Research Laboratories, Rahway, NY. pp. 326–327.

*Primary Examiner*—Raj Bawa
*Attorney, Agent, or Firm*—McAulay Nissen Goldberg Kiel & Hand, LLP

[57] ABSTRACT

A method for treating allergic rhinitis in a patient is disclosed which comprises applying an anti-allergic rhinitis effective amount of a steroid in ointment or creme carrier to the lining of the vestibules of the patient.

10 Claims, No Drawings

METHOD OF TREATING ALLERGIC RHINITIS BY DELIVERING MEDICATION VIA THE NASAL VESTIBULES

FIELD OF THE INVENTION

This invention relates generally to a delivery system for allergy medication and its use. The invention also relates to medication formulations for use in the delivery system.

BACKGROUND OF THE INVENTION

Seasonal allergic rhinitis is a problem that many people deal with every year. Common characteristics of this disease are a runny nose, constant sneezing, watery eyes, and general discomfort. Irritation causes itchiness within the nose which is followed by the symptoms mentioned above. Nasal spray and oral medications are presently the most commonly used in medication preventative and ameliorative care, but they are not always effective in treating allergic rhinitis in patients. Oral medication is not effective for all allergy sufferers, may make the patient drowsy and requires substantial delay before taking effect. Nasal sprays deliver the medication deeply into the nasal cavity, for example, into the atrium and nasal concha. However, if the patient has excessive nasal drip, the medication may not be absorbed at its target but will flow out of the nostril with the nasal fluid.

SUMMARY OF THE INVENTION

We have discovered an effective method for the rapid relief of the symptoms associated with seasonal allergic rhinitis. This is accomplished by application of an appropriate anti-allergy medicament to the vestibules of the nostrils. The general chain of events of seasonal allergic rhinitis begins with itchiness in the nose, especially in the vestibules, and continues with a runny nose and sneezing. We have discovered that by application of the medicament to the vestibules manually, e.g., with the tip of a finger or a padded cotton swab, rapid cessation of the symptoms, e.g., runny nose, watery eyes, sneezing and the like can be achieved.

As used herein, vestibule of the nose refers to the slight dilatation of the nostril interior to the naris, or opening of the nostril to the atmosphere. The vestibule is bounded laterally by the ala and lateral crus of the greater alar cartilage and medially by the medial crus of the same cartilage. The vestibule is lined by skin containing hairs and sebaceous glands and extends as a small recess toward the apex of the nose.

More particularly, we have discovered that a variety of medical agents which generally are indicated as being anti-inflammatory are used for topical applications to the skin for inflammation can be used as the medicament with the present invention. Suitable for use are steroids in ointment or cream carrier. Such ointments or cremes are tactile to the surface of the vestibule and do not readily flow out of the nostril.

Prior art methods of nasal steroid delivery for treating allergic rhinitis are exclusively targeted to the mucous membranes found deeply inside the nasal cavity, while the instant delivery method is targeted primarily to the vestibule. The prior art steroid ointments and cremes have been used only for the alleviation of allergic reactions on the skin, and nothing has heretofore suggested their use in stopping the cascade of symptoms in allergic rhinitis.

In more severe cases of allergic reactions, repeated applications of the steroid may be needed before complete relief is achieved. In the most severe cases, relief can be obtained by following one or more of the applications with isolated pressure or massage into the vestibule. The pressure or massage helps to enable the medication to reach the vestibule epithelium in order to have its ameliorative effect and helps prevent the washing out of the medication with the excessive nasal fluid of a severe allergic reaction. This pressure can be applied, for example, by lightly pressing or even lightly rubbing against the wall of the vestibule. A finger, padded cotton swab or other suitable implement may be used to apply the pressure or perform the rubbing.

In cases of severe allergic reactions causing excessive nasal fluid discharge, an optional step of temporarily stopping the fluid flow through the vestibule or drying out of the vestibule may be performed before the steroid ointment or creme is applied. A temporary cessation of fluid flow through the nose can often be achieved by applying pressure to and/or gently pulling down on the area of skin just below the nose and above the upper lip. A temporary drying out of the vestibule may be achieved, for example, by using absorbent materials in the vestibule, such as a cotton swab, or removing the fluid through gentle suction. Any other known means for the temporary cessation of fluid flow through the vestibule of the nostril may be used.

As medical agents for use in the inventive method, steroids or steroid mixes known to relieve irritations of skin surfaces or the nasal mucosa may be used for delivery according the method of the invention. Preferably, corticosteroids are used and most preferably, glucocorticosteroids. Examples of steroids for use in the method include, but are not limited to, flunisolide, triamcinolone, beclomethasone dipropionate, fluticasone propionate and budesonide. Other allergy medicaments such as anti-cholinergics such as ipratropium bromide or antihistamines such as Azelastin may also be formulated for the delivery method of the invention. In fact, any active ingredient of a liquid nasal spray for treating allergic rhinitis may be advantageously applied according to the invention by incorporating it in a suitable emollient.

It is also possible to apply an antibiotic in ointment or liquid form to the vestibule before, with or after application of the medical agent for cleansing or antiseptic purposes.

One of skill in the art of topical steroid medications would well know how to make formulations for use with this delivery method, based on well known methods of making, stabilizing and storing steroid ointments and cremes. Likewise, emollients for forming medical cremes and ointments are well known in the art. One of skill in the art of pharmacology would well know how to determine the dose of medicament to be applied, based on well known dosages for treating other epithelial rashes or irritations.

The present invention is illustrated, but not limited, by the following Examples.

EXAMPLE 1

During the grass season in 1996, a 54 year old male patient experienced a severe nasal allergy attack. Intranasal steroid spray were ineffective to relieve the allergies but the medication simply dripped out of the nostril. A predenicarbate cream was applied to the inner surface of the vestibules and repeated this several times while applying local pressure to the vestibules. Within one half to one hour, allergic symptoms ceased.

EXAMPLE 2

At the end of May 1996, a 54 year old male, who is allergic to grass, played golf while a lawn mower cut the grass. One half hour prior to playing golf, Triamcinolone solution mixed with Vaseline was applied to inner surface of the vestibules. As a result, the patient was able to finish an entire eighteen holes of golf without experiencing violent itching of the vestibules or sneezing.

EXAMPLE 3

A 55 year old female who has a history of perennial rhinitis and is allergic to pollen/grass and extremely sensitive to temperature change. She suffered a moderate pollen allergy attack of a runny nose and constant sneezing at the end of May 1997. Because oral medication proved ineffective in improving her condition, liquid Ipratropium was applied to the inner vestibules. Her runny nose stopped temporarily, but after doing some housework her nose began to run again. She then applied a mixture of Beclomethasone liquid and Vaseline ointment into inner vestibules. Within an hour, her runny nose stopped.

EXAMPLE 4

A 24 year old female experienced allergies on two consecutive mornings. Her vestibules felt itchy, causing mucous production in her nose. Triamcinolone ointment was applied and rubbed it into the vestibules. After approximately one hour, the itchiness subsided and mucous flow disappeared. She also applied this ointment the following morning. Although the mucous secretion and itchiness within the vestibules did not subside as quickly as it had formerly, the allergies eventually subsided within a short time.

What is claimed is:

1. A method for treating allergic rhinitis in a patient consisting essentially of topically manually applying a composition in the form of an ointment or creme, wherein the composition contains an anti-allergic rhinitis effective amount of a medical agent selected from the group consisting of steroids, antihistamines and anti-cholinergics in a topical carrier to the lining of the nasal vestibules of the patient.

2. The method of claim 1 wherein the medical agent is a steroid.

3. The method of claim 1 wherein the medical agent is an antihistamine.

4. The method of claim 1 wherein the medical agent is an anti-cholinergic.

5. The method of claim 1 wherein an antibiotic in liquid or ointment form is applied for cleansing or antiseptic purposes.

6. The method of claim 1 wherein the medical agent is selected from the group consisting of flunisolide, triamcinolone, beclomethasone dipropionate, fluticasone propionate and budesonide, ipratropium bromide and Azelastine.

7. The method of claim 1, further comprising applying localized pressure or massage to the lining after application of the steroid.

8. The method of claim 1, wherein the steroid is repeatedly applied.

9. The method of claim 8, wherein after each application of steroid, localized pressure or massage is applied to the lining.

10. The method of claim 1 wherein the medical agent is applied by fingertip or cotton swab.

\* \* \* \* \*